United States Patent
Lamartine et al.

(10) Patent No.: US 9,241,555 B2
(45) Date of Patent: Jan. 26, 2016

(54) HAIR TREATMENT DEVICE FOR PROVIDING DISPERSED COLORS BY LIGHT DIFFRACTION

(71) Applicants: The Procter & Gamble Company, Cincinnati, OH (US); Los Alamos National Security, LLC, Los Alamos, NM (US)

(72) Inventors: Bruce Carvell Lamartine, Los Alamos, NM (US); E. Bruce Orler, Blacksburg, VA (US); Richard Matthew Charles Sutton, Cincinnati, OH (US); Shuangqi Song, Houston, TX (US)

(73) Assignees: The Procter & Gamble Company, Cincinnati, OH (US); Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 14/081,671

(22) Filed: Nov. 15, 2013

(65) Prior Publication Data

US 2014/0069454 A1    Mar. 13, 2014

Related U.S. Application Data

(63) Continuation of application No. 13/248,746, filed on Sep. 29, 2011, now Pat. No. 8,607,803.

(51) Int. Cl.
| | | |
|---|---|---|
| A45D 1/06 | (2006.01) | |
| A45D 1/12 | (2006.01) | |
| A61Q 5/06 | (2006.01) | |
| A61K 8/81 | (2006.01) | |
| A61K 8/85 | (2006.01) | |
| A61K 8/87 | (2006.01) | |
| A61K 8/18 | (2006.01) | |

(52) U.S. Cl.
CPC .. *A45D 1/06* (2013.01); *A45D 1/12* (2013.01); *A61K 8/18* (2013.01); *A61K 8/8129* (2013.01); *A61K 8/8152* (2013.01); *A61K 8/85* (2013.01); *A61K 8/87* (2013.01); *A61K 2800/437* (2013.01); *A61K 2800/80* (2013.01); *A61Q 5/065* (2013.01)

(58) Field of Classification Search
CPC ............ A45D 1/00; A45D 1/02; A45D 1/04; A45D 1/06; A45D 1/16; A45D 2001/004; A45D 2/00; A45D 2/001; D06F 75/30; B29C 66/861; B29C 66/8612; B29C 66/8614
See application file for complete search history.

(56) References Cited

U.S. PATENT DOCUMENTS

| | | | |
|---|---|---|---|
| 6,583,933 B2 | 6/2003 | Lamartine | |
| 6,822,030 B2 | 11/2004 | Olson | |
| 6,855,371 B2 | 2/2005 | Gler | |
| 7,083,805 B2 | 8/2006 | Begleiter | |
| 7,625,513 B2 | 12/2009 | Yu | |
| 8,016,585 B2 * | 9/2011 | Komoriya et al. | ............ 425/385 |

(Continued)

FOREIGN PATENT DOCUMENTS

| | | |
|---|---|---|
| EP | 0524346 B1 | 6/1998 |
| JP | 2010030920 A1 | 2/2010 |
| WO | WO2011160098 A2 | 12/2011 |

*Primary Examiner* — Robyn Doan
*Assistant Examiner* — Tatiana Nobrega
(74) *Attorney, Agent, or Firm* — James T. Fondriest

(57) ABSTRACT

Hair was coated with polymer-containing fluid and then hot pressed to form a composite of hair and a polymer film imprinted with a nanopattern. Polychromatic light incident on the nanopattern is diffracted into dispersed colored light.

3 Claims, 8 Drawing Sheets

(56) References Cited

U.S. PATENT DOCUMENTS

| | | |
|---|---|---|
| 2002/0159965 A1 | 10/2002 | Frechet |
| 2007/0141002 A1 | 6/2007 | Montezinos |
| 2008/0019925 A1* | 1/2008 | Begleiter ..................... 424/10.2 |
| 2008/0312395 A1 | 12/2008 | Muller |
| 2009/0186055 A1 | 7/2009 | Dumousseaux |
| 2009/0264836 A1 | 10/2009 | Roe |
| 2010/0086801 A1 | 4/2010 | Russell |
| 2010/0120116 A1* | 5/2010 | Kaplan et al. ................. 435/180 |
| 2010/0135918 A1 | 6/2010 | Kim |
| 2010/0139681 A1 | 6/2010 | Oshika |
| 2010/0263683 A1 | 10/2010 | Dutheil-Gouret |
| 2010/0307553 A1 | 12/2010 | Defries |
| 2011/0135697 A1 | 6/2011 | Omenetto |
| 2013/0000661 A1 | 1/2013 | Fondin |
| 2013/0052419 A1 | 2/2013 | Yializis |
| 2013/0255715 A1* | 10/2013 | Lund et al. .................... 132/225 |

* cited by examiner

Sawtooth master pattern used for nanoimprinting polymer coated hair

Pitch: 1667 – 3333 nm
Depth: 200 – 400 nm

Motheye structure:
Rectangular pits with different pitch in vertical and horizontal directions

HAIR TREATMENT DEVICE FOR PROVIDING DISPERSED COLORS BY LIGHT DIFFRACTION

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to providing hair with a nanopatterned film that produces colors by diffracting incident light.

BACKGROUND OF THE INVENTION

Almost all hair coloring methods use colorants (dyes, for example) that change the color of the hair and produce a single color from the treated hair. Coloring methods include methods for permanent coloring and methods for temporary coloring.

Permanent coloring methods typically use ammonia to open up a hair cuticle so that colorants may be deposited on the underlying hair cortex. Peroxide is used to remove existing natural and artificial pigments.

Temporary methods also use colorants such as acidic dyes that do not significantly penetrate the cuticle. Temporary methods also don't use ammonia. Shampooing eventually washes out temporary colorants and the hair's natural pigment is retained. Ground silica suspended in a polymer has also been used to create a temporary iridescent effect.

Fiber coloration with little or no colorants occurs in nature. Peacock feathers, for example, are known to have little or no pigmentation. The striking colors in peacock feathers are produced primarily from diffraction of incident light from nanometer scale branches of the peacock feathers.

SUMMARY OF THE INVENTION

To achieve the foregoing and other objects, and in accordance with the purposes of the present invention, as embodied and broadly described herein, the present invention provides a hair treatment process. The process involves coating hair with a polymer-containing fluid of a suitable soluble (and/or dispersible) polymer and inserting the coated hair into a pressing device capable of both transforming the fluid into a film and forming on a surface of the film a nanostructured pattern suitable for producing colors by light diffraction. Preferably, the hair is cleaned and dried before coating the hair with the fluid. The fluid optionally includes a plasticizer. Optionally, the fluid includes a surfactant. The fluid-coated hair is pressed under conditions suitable for forming the film having the nanostructured pattern. The hair and film are cooled and removed from the device. Exposure of the coated hair to incident polychromatic light (e.g. sunlight, theatrical light) results in dispersed colored light from light diffracted from the film.

The invention is also concerned with a hair treatment process that provides hair with a diffractive coating. The process includes coating hair with a fluid including a polymer that has a glass transition temperature from about 55 degrees Celsius to about 90 degrees Celsius. Preferably, the hair is clean and dried before coating the hair with the solution. Optionally, the fluid includes a plasticizer. Optionally, the fluid includes a surfactant. The fluid-coated hair is inserted into a pressing device having a block with a nanostructured pattern under conditions suitable for forming a film with a nanostructured pattern complementary to the pattern from the block. The fluid-coated hair is hot pressed under conditions suitable for forming the film with the nanostructure pattern. After cooling the hair and film, the hair and film are exposed to incident light, which results in dispersed colored light diffracted from the film.

The invention is also concerned with a heating iron for treating hair. The heating iron includes all of the elements of a conventional heating iron with the exception of a heating block that has been configured with a nanostructured surface suitable for forming a complementary nanostructured pattern in a flexible film formed when a sample of hair coated with a fluid including a polymer with a glass transition temperature of from about 55 degrees Celsius to about 90 degrees Celsius is hot pressed using the heating block.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

Figure 1:
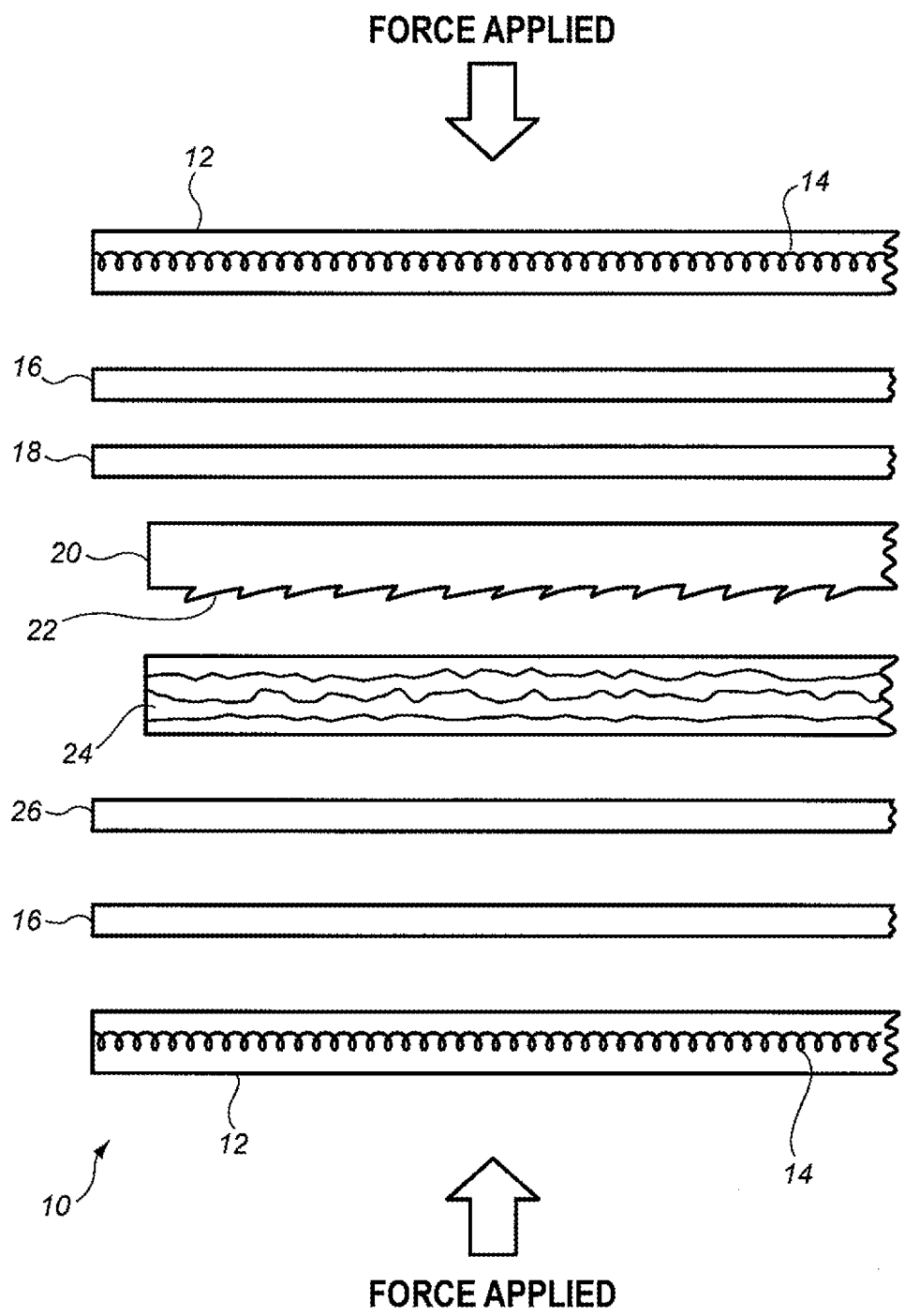
FIG. 1 shows a sketch of hot-pressing a sample of fluid-coated hair according to an embodiment of the invention.

This invention relates to a method and apparatus for treating hair. Hair treated by the method becomes coated with a polymer film that diffracts light to produce dispersed colored light. In an embodiment, a color spectrum results from light diffraction from a nanometer-scale pattern imprinted onto a polymer film coated onto the hair. The nano-pattern is formed by coating the hair with a fluid that includes a polymer and hot pressing the fluid-coated hair under a few pounds per square inch (psi) pressure using a hot press that includes a suitably modified heating block capable of forming nano-patterns in the polymer film. The method provides a temporary coloration effect because the polymer can be shampooed out of the hair.

The nano-patterned block can be incorporated into a handheld device similar to a common hair flatiron. A nano-patterned block may be suitably configured to provide a nanostructured pattern in film coated hair to produce a rainbow of colors. A nano-patterned block can also be suitably configured to produce directionally specific images in the polymer coated hair.

The net effect of applying the method to hair is that when the hair changes position relative to a dominant light source, such as sunlight or theatrical lights, the hair color and any images incorporated into the hair change as well.

Different nano-patterned blocks may be used for different multiple color or image effects in the treated hair.

The hair treatment method forms a composite of hair and polymer-containing film and creates a nanostructured pattern in the film that produces dispersed colored light. Suitable polymers useful with this invention are soluble and/or dispersible in water or alcohol, do not damage the hair, and have a glass transition temperature (Tg) in a range such that a film can be formed when a fluid including polymer is coated onto the hair, then hot-pressed and converted into a film with a nanostructured pattern that diffracts light into dispersed colored light. The temperatures used for hot pressing the solution-coated hair should be above the glass transition temperature (Tg) of the polymer. In an embodiment, the pressing temperature is 20 to 30 degrees higher than the glass transition temperature of the polymer. The fluid and polymer therein should flow to conform to the nanostructured features of the nanostructured block of the hot pressing device. A suitable range for Tg of the polymer is a range from about 55 degrees Celsius to about 90 degrees Celsius.

Suitable polymers with a Tg from about 55 degrees Celsius to about 90 degrees Celsius include, but are not limited to, a poly-lactic acid, a polyvinyl alcohol, acrylic acids, acrylates, polyurethanes, copolymers thereof, and mixtures thereof.

The fluid may be a polymer-containing solution. The fluid may be a polymer-containing suspension. The fluid may be a polymer-containing dispersion, such as a polymer-containing emulsion. The invention has been demonstrated using a fluid that is a commercially available polymer-containing dispersion. The polymer-containing fluid may include a plasticizer. The polymer-containing fluid may include a surfactant. The polymer-containing fluid may include an emulsifier. These additional components may be optional components of the fluid so that it is suitable for coating the hair and for the subsequent heating that transforms the fluid into a film with a surface imprinted with a nanostructured pattern capable of diffracting incident light into dispersed colors that are visible on the film-coated hair.

The film-coated hair after heat treatment may be thought of as a composite of the hair and the polymer-containing film that diffracts incident polychromatic light into dispersed colors.

The polymer-containing fluid typically includes a liquid chosen from water (providing a aqueous polymer-containing solution), an alcohol (e.g. ethanol), or mixtures of water and alcohol.

No dyes are required for the heat treatment process because the color results from diffraction of light and not from any dye. Color can be removed by wetting or shampooing the treated hair.

Suitable polymers are polymers that are removable from the hair by wetting or shampooing. These include, but are not limited to, polymers such as polyvinyl alcohol, acrylates, and polylactic acid that are soluble and/or dispersible.

An embodiment device for treating hair includes a standard hair press with a nano-patterned thermal block inserted into the hair press. After forming a composite of the hair with the polymer, the composite is treated using the hair iron by hot pressing. The result of the treatment is a thin film composite of hair and polymer that diffracts light to produce color.

An embodiment nano-patterned thermal block may be prepared using any known method and device for such as, but not limited to, focused ion beam (FIB), photonic lithography, e-beam lithography, tool machining, ruling engines, diamond turning devices, and any other method or device that can produce nanometer scale features.

FIG. 1 shows a sketch of hot pressing a sample of fluid-coated hair according to an embodiment of the invention. The hot press 10 includes press jaws 12 and heating element 14 for heating the jaws 12. As FIG. 1 shows, adjacent each of jaws 12 is a platen 16. Adjacent one of platens 16 is a backing layer 18 such as a layer of a heat-resistant commercially available polymer such as but not limited to TEFLON. Adjacent the backing layer 18 is heating block 20 configured with a nano-patterned surface 22 facing fluid-coated hair sample 24. The fluid-coated hair sample 24 is coated with the polymer-containing fluid that may optionally include one or more of a plasticizer, a surfactant, and an emulsifier. The fluid may be a dispersion containing a polymer, a plasticizer, a surfactant, and an emulsifier. Backing layer 26 (e.g. aluminum foil) adjacent sample 24 and platen 16, which is adjacent press jaw 12. FIG. 1 shows force being applied to jaws 12 in order to press the jaws 12 together, which squeezes together all elements in between the jaws (i.e. platens 16, backing layer 18, heating block 20 with surface 22, sample 24, and backing layer 26) while an electric current is sent to heating element 14, which heats the jaws 12 and makes the pressing a hot pressing. Enough current is sent to heat the device to a temperature suitable for forming a film imprinted with the nano-patterned surface 22 of heating block 20. As the sample of coated hair 24 is hot-pressed, a film forms with a surface imprinted with a nanopattern that complements the nanopatterned surface 22 facing the sample. The pressing is continued for a suitable time, pressure, and temperature until the fluid that coats the hair conforms to the nanopatterned surface 22 so that a film having this nanopatterned surface may be formed that will diffract incident polychromatic light into dispersed colors of light. After the hot pressing, the pressing force is discontinued. The pressed sample is removed from the hot press and allowed to cool.

Figure 2:
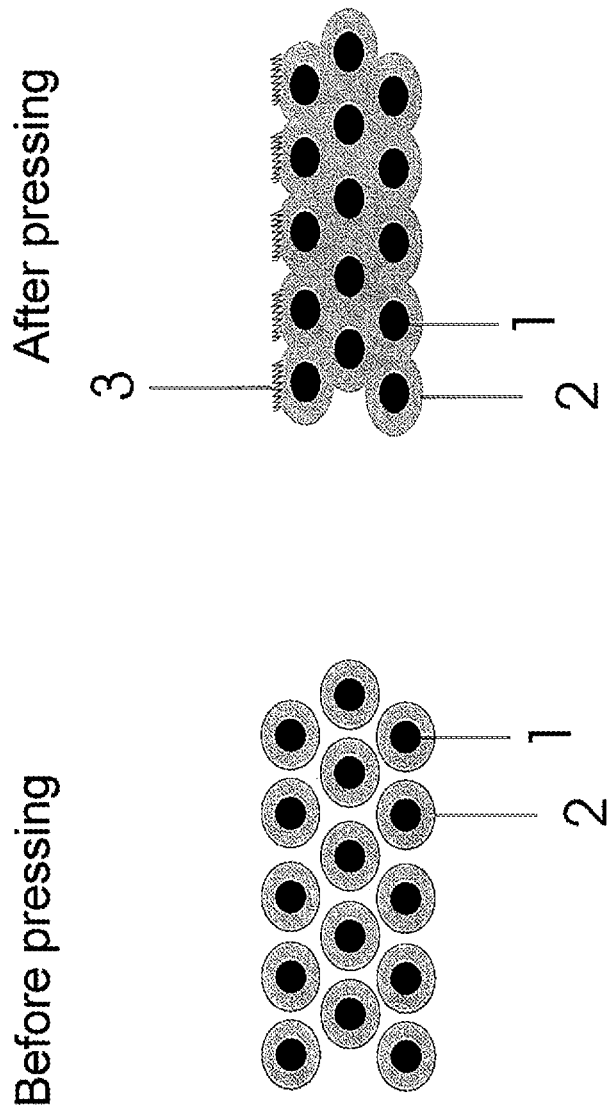
FIG. 2a shows a sketch of details of magnified fluid-coated hair prior to hot pressing.
FIG. 2b shows a sketch of the hair after hot pressing to form film with a nanostructured pattern that diffracts polychromatic light, producing dispersed colors.

FIG. 2a shows a "before pressing" sketch of details of magnified fluid-coated hair prior to hot pressing, and FIG. 2b shows an "after-pressing" sketch of the hair after hot pressing to form film with a nanostructured pattern that diffracts light. The sketches are cross-sectional views. FIG. 2a shows individual strands from the hair sample coated with the polymer-containing fluid. The hair shafts 1 are each coated with the polymer-containing fluid 2. There is space in between individual strands of coated hair. A result of hot pressing is a film that binds the individual hairs into a composite (FIG. 2b). As FIG. 2b shows, surface portions of the polymer film are imprinted from the heating block surface 22 with a nanopattern 3 that diffracts incident polychromatic light into dispersed colors.

Figure 3:
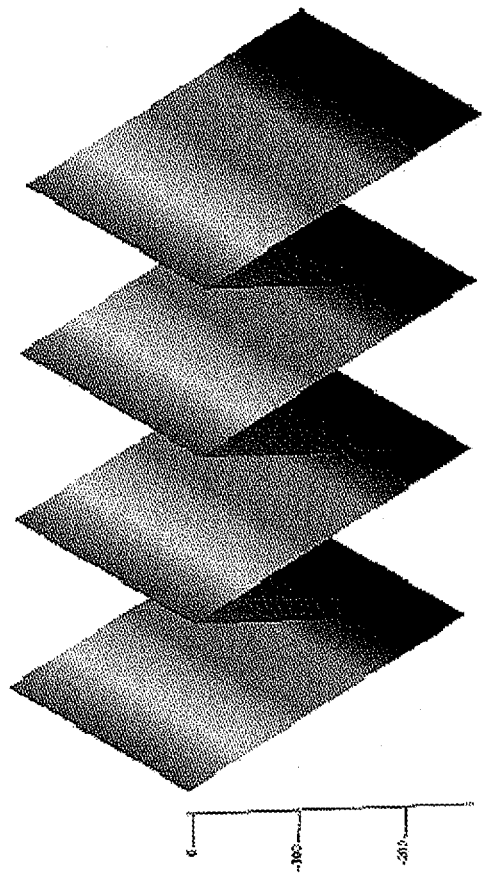
FIG. 3 shows a sketch of a sawtooth pattern that was formed in film coated hair that was shown to form dispersed colored light upon interaction with sunlight and theatrical light.

In an embodiment, a nanopatterned heating block 22 with a sawtooth pattern was prepared and used to prepare a diffractive film from fluid-coated hair. A metal block with a sawtooth pattern was prepared using a scribe machine to mill a sawtooth pattern into a metal blank. A soda-lime glass casting of the patterned metal was then used as the heating block. The hair sample was human hair that had been cleaned and dried. The hair sample was hot pressed at a pressure of about 3-7 psi at a temperature above the glass transition temperature of the polymer. The result was a composite film including hair and polymer. The nanostructured block imprinted a complementary sawtooth pattern into the film, shown in FIG. 3. This pressed sample was demonstrated to form dispersed colors of light from polychromatic sunlight and theatrical light incident upon the sawtooth-patterned surface of the film.

A variety of other nano-patterned thermal blocks were prepared using a focused ion beam (FIB). FIB pattern generator control files were written for this purpose of forming nanopatterns suitable for light diffraction of incident polychromatic light.

Figure 4A:
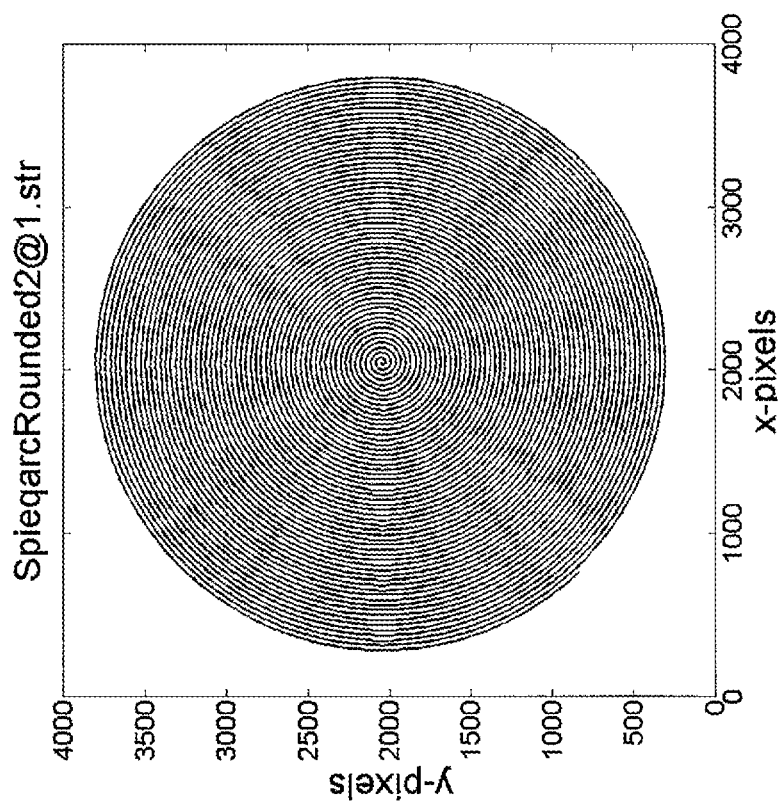
FIGS. 4a through 4e show nanopatterns including a spiral, parabola, and hyperbola that were milled into blanks to make embodiment heating blocks that were imprinted into polymer films that form dispersed colored light from incident polychromatic light such as sunlight and theatrical light.
Figure 4B:
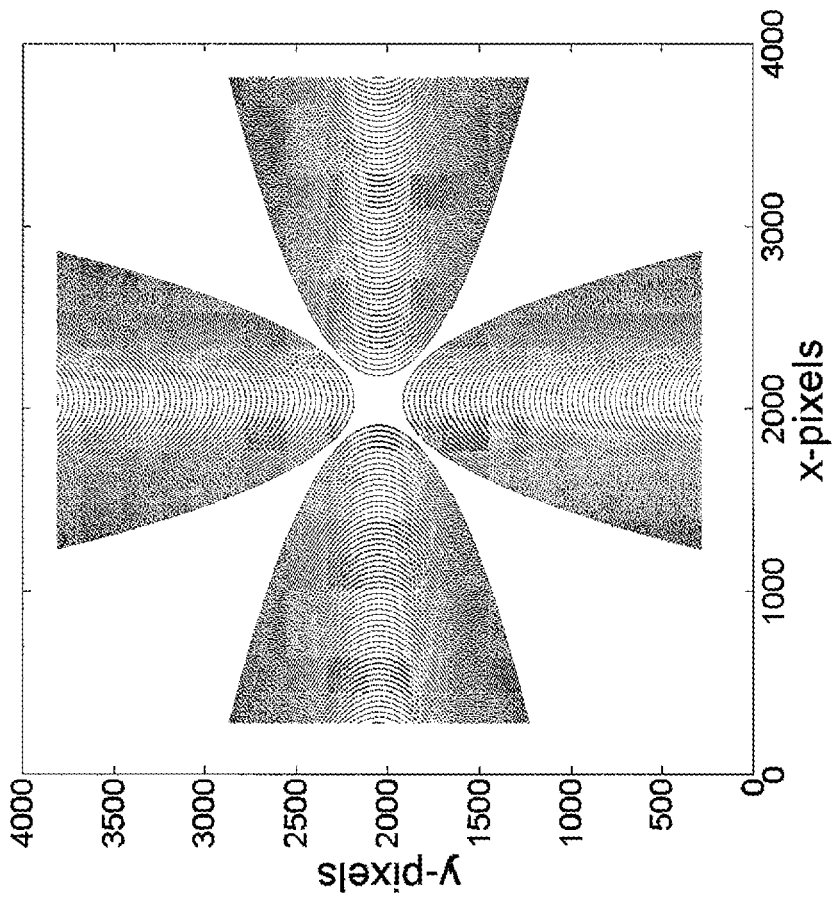
Figure 4C:
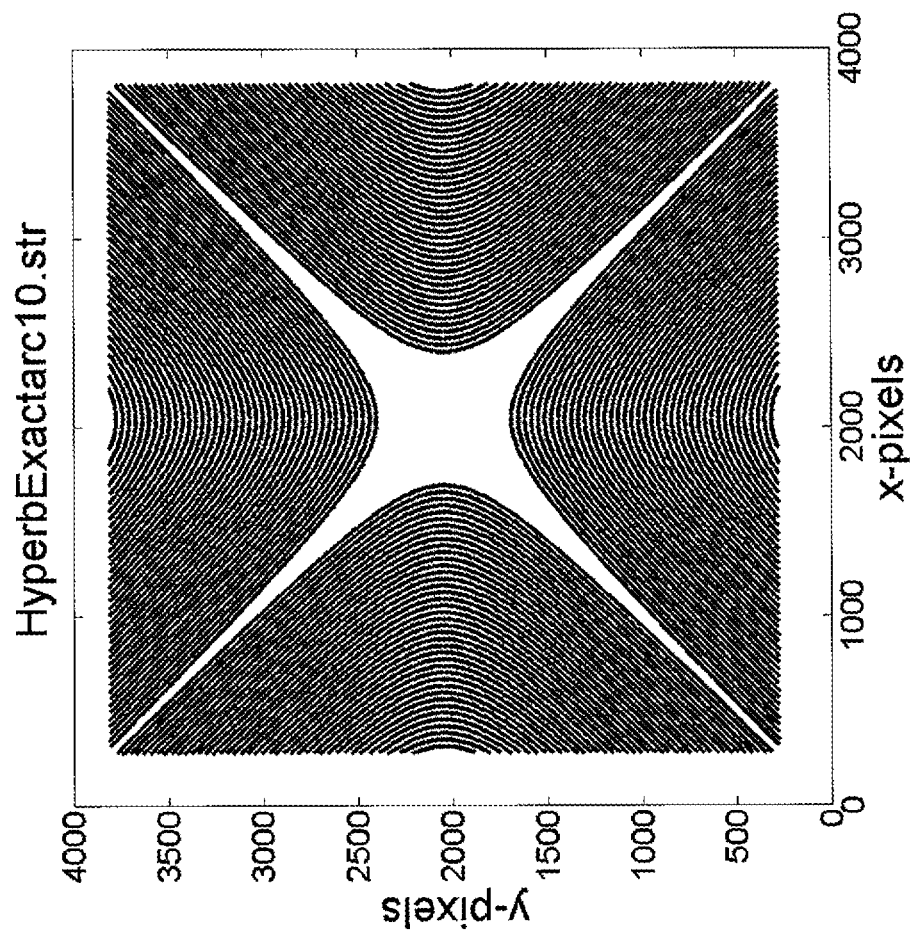
Figure 4D:
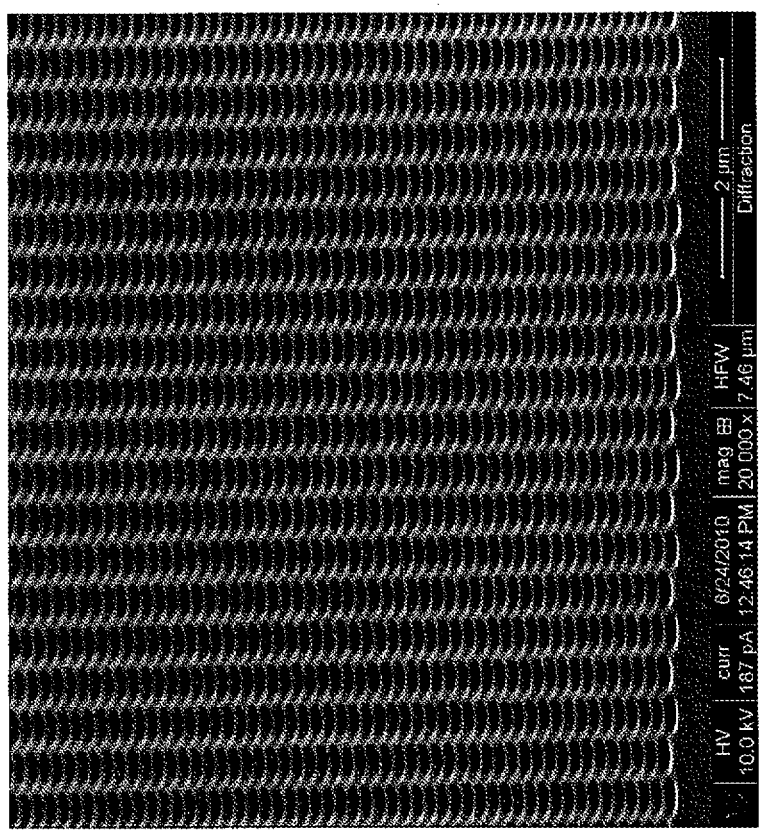
Figure 4E:
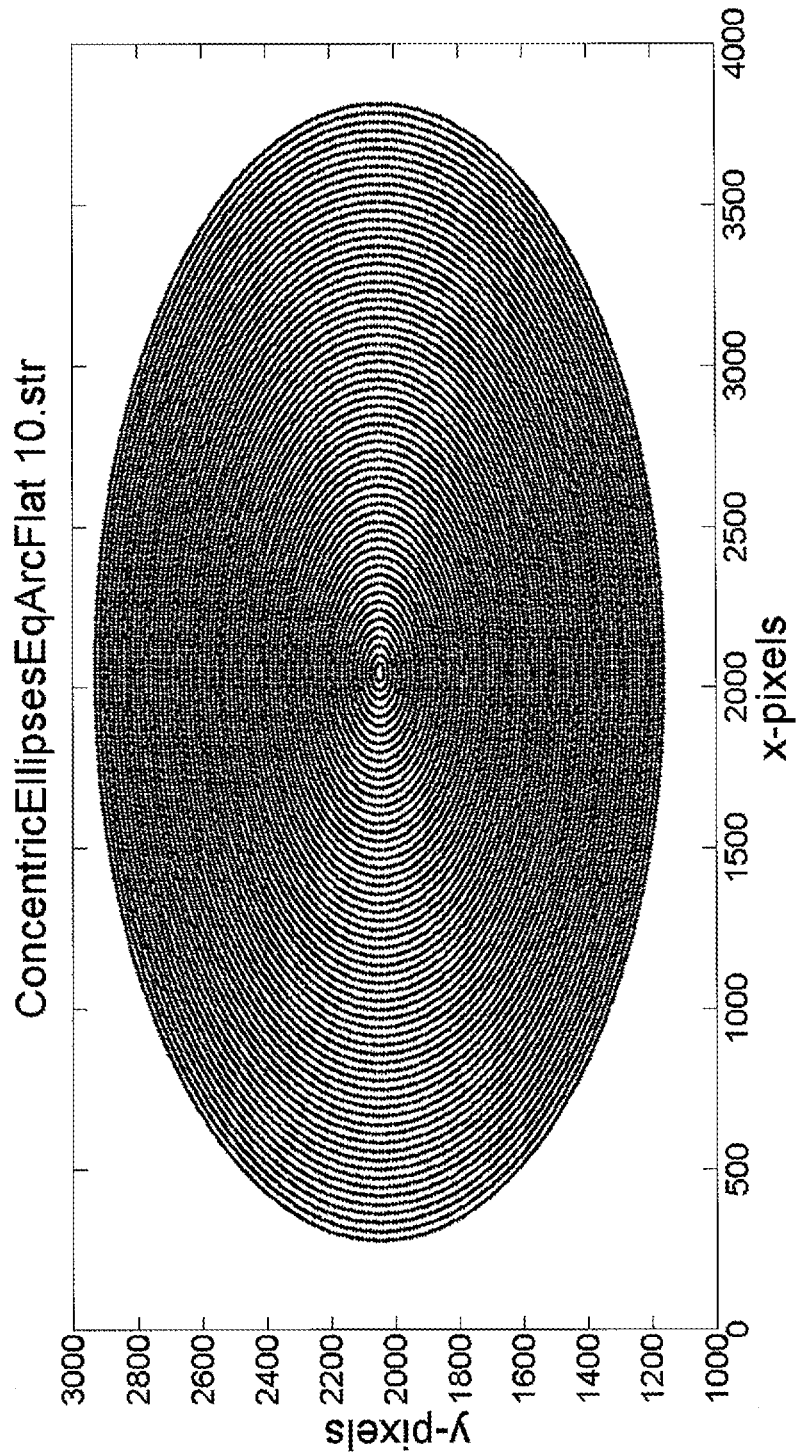

FIGS. 4a through 4e shows show several nanopatterns that were prepared and were imprinted into a surface of a polymer film that was not coated onto hair. FIG. 4a shows a spiral pattern with a circular envelope that was milled to form a patterned block using the pattern generator control file SpieqarcRounded2@1.str. FIG. 4b shows a nanopattern of concentric parabolic rings made using the pattern generator control file ParabExactArc10.str. FIG. 4c shows a nanopattern of concentric hyperbolic rings made using the pattern generator control file HyperpbExactarc10.str. FIG. 4d shows a moth-eye pattern of rectangular pits with different pitch in vertical and horizontal directions made using the pattern generator control file Smotheye2@30.str. FIG. 4e shows a spiral with an elliptical envelope made using the pattern generator control file ConcentricEllipsesEqArcFlat10.str. Each of the nanopatterns was milled into a metal blank to produce a nanopatterned heating block that was imprinted into a polymer film that diffracts incident polychromatic light into dispersed colors. It is believed that hair provided with these types of films with these nanopatterns will diffract incident polychromatic light into dispersed colors.

A description of how FIB has been used for milling three-dimensional features on nanometer scale into media such as metal can be found in U.S. Pat. No. 5,773,116 and U.S. Pat. No. 5,721,687, both incorporated by reference. U.S. Pat. No. 6,583,933, incorporated by reference, also describes milling using a FIB to form aggregates of pits of low symmetry that produce directional diffraction gratings with blaze emphasizing a particular arbitrary spectral range.

A mastering process similar to that used for CDROM replication may be used to prepare nano-patterned heating blocks after first preparing a master block. To prepare the master block, a mill pattern is written for a FIB milling device and applied to a master blank to convert the master blank into a master for the heating block. The master blank may be a metal blank made from a metal such as nickel, titanium, aluminum, tungsten, silicon, and the like. The master block is used to prepare the nano-patterned heating block. Heating blocks may be made of, for example, soda lime glass.

It is envisioned that a commercially available heating hair iron, such as one made by CHI or BABYLISS, could be modified according to an embodiment of this invention, by replacing a heating block in the commercially available hair iron with a heating block suitably configured with a nanopattern such as the aforementioned sawtooth nanopattern or some other nanopattern such as a nanopattern shown in FIG. 4. A nano-patterned heating block prepared by FIB milling, or by some other process for creating suitable nanopatterns, could be used to modify the heating block of the commercially available heating device. Alternatively, a blank heating block adapted to fit into the commercially available heating iron could be milled with a nanopattern suitable for heating solution-coated hair and imprinting a complementary nanopattern into the resulting film. It is envisioned that a commercially available heating iron, such as one made by CHI or BABYLISS, could be modified to produce an embodiment apparatus that could treat fluid-coated hair according to the aforementioned process for providing hair with a film imprinted with a nanopatterned surface that would diffract incident polychromatic light into dispersed colors. This way, a person could treat their own hair or another person's hair according to an embodiment of this invention and provide their own hair or another person's hair with a nanopattern-imprinted polymer-containing film that diffracts polychromatic light such as sunlight or theatrical light into dispersed colored light.

The method of the invention was demonstrated using human hair and commercially-available polymer-containing fluids known by the commercial name KOLLICOAT MAE 100P. These fluids are dispersions that are reported to include a 1:1 copolymer of methacrylic acid and ethyl acrylate. They have been reported to also include sodium laurate and polysorbate 80, which are a surfactant and emulsifier derived from polyethoxylated sorbitan and oleic acid. Samples of human hair were mixed with the KOLLICOAT MAE 100P. In one embodiment, an 18% by weight dispersion of KOLLICOAT MAE 100P in water was used to prepare a hair-polymer film composite having a thickness of 13 micrometers. In another embodiment, a 4.2% by weight dispersion of KOLLOCOAT MAE 100P in ethanol with 10% triethyl citrate plasticizer was used to prepare a hair-polymer film composite having a thickness of 3-4 micrometers. Each of the films after hot pressing with a nanopatterned heating block diffracted polychromatic light into dispersed colors.

It should be understood that the invention is not to be limited to using any particular polymer-containing fluid with any particular added components of plasticizers, surfactants, emulsifiers, and the like, and that any polymer-containing fluid suitable for forming a film on the hair after hot pressing to conforms to a suitable nanopattern in a heating block falls within the scope of this invention.

The invention is not limited to any particular nanopattern. Patterns may be produced according to fashion whim. Suitable nanopatterns are any that are capable of diffracting polychromatic light into dispersed colors of light.

An embodiment of the treatment may provide color images that appear momentarily as the hair moves on the head. Movement of the head results in changing the relationship between the film-coated hair and someone looking at the hair. A person looking at the hair detects the dispersed colors, which appear when the angle of reflection of the incident light permits the viewer to observe the dispersion of the colors.

The method of hair treatment is an example of a temporary method because polymers that are soluble and/or dispersible polymers are chosen for the process. Thus, the color is removed when the hair is cleaned by shampooing, which dissolves the polymer, which removes the nanopattern.

This process for hair treatment provides a means for arbitrary directional control of color reflected from illuminated hair, and for embedding local iridescent color regions into hair using suitable nanopatterns that diffract light into dispersed colors.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A handheld heating iron for treating hair, the heating iron comprising a heating block suitably configured for the heating iron, the heating block comprising a nanostructured surface pattern suitable for forming a complementary nanostructured surface pattern in a hair-polymer film composite, where the nanostructured surface pattern is milled onto the surface of the heating block and the heating iron is a hair heating iron comprising two press jaws with a heating element inside the press jaws and the heating block is coupled to one of the press jaws such that the heating element thereof heats the heating block.

2. The heating iron of claim 1, wherein the nanostructured surface pattern comprises a pattern selected from the group consisting of spiral patterns, archimedean patterns, ellipsoidal patterns, patterns having hyperbolic rings, patterns having parabolic rings, and combinations thereof.

3. The heating iron of claim 1, wherein the nanostructured surface pattern comprises a sawtooth pattern and/or a ring pattern.

* * * * *